United States Patent
Averbuch et al.

(10) Patent No.: US 11,024,026 B2
(45) Date of Patent: *Jun. 1, 2021

(54) ADAPTIVE NAVIGATION TECHNIQUE FOR NAVIGATING A CATHETER THROUGH A BODY CHANNEL OR CAVITY

(71) Applicant: COVIDIEN LP, Mansfield, MA (US)

(72) Inventors: Dorian Averbuch, Ramat HaSharon (IL); Oren Weingarten, Herzliya (IL); Leo Joskowicz, Jerusalem (IL); Igor Markov, Hod HaSharon (IL); Ivan Vorobeychyk, Petah Tikva (IL); Ran Cohen, Petah Tikva (IL)

(73) Assignee: COVIDIEN LP, Mansfield, MA (US)

( * ) Notice: Subject to any disclaimer, the term of this patent is extended or adjusted under 35 U.S.C. 154(b) by 168 days.

This patent is subject to a terminal disclaimer.

(21) Appl. No.: 16/445,887

(22) Filed: Jun. 19, 2019

(65) Prior Publication Data

US 2019/0304091 A1    Oct. 3, 2019

Related U.S. Application Data

(63) Continuation of application No. 15/635,390, filed on Jun. 28, 2017, now Pat. No. 10,346,976, which is a
(Continued)

(51) Int. Cl.
*G06T 7/00* (2017.01)
*G06T 7/60* (2017.01)
(Continued)

(52) U.S. Cl.
CPC ............ *G06T 7/0012* (2013.01); *A61B 34/10* (2016.02); *A61B 34/25* (2016.02); *G06T 7/11* (2017.01);
(Continued)

(58) Field of Classification Search
CPC ... A61B 34/10; A61B 34/25; A61B 2034/107; A61B 2034/252; A61B 2090/3762;
(Continued)

(56) References Cited

U.S. PATENT DOCUMENTS 5,078,150 A   1/1992   Hara et al.
5,480,422 A   1/1996   Ben-Haim
(Continued)

FOREIGN PATENT DOCUMENTS

WO    2006076789 A1    7/2006

OTHER PUBLICATIONS

Konishi et al. "Augmented reality navigation system for endoscopic surgery based on three-dimensional ultrasound and computed tomography: Application to 20clinical cases." International Congress Series. vol. 1281. Elsevier, 2005. (Year: 2005).
(Continued)

*Primary Examiner* — Katrina R Fujita
(74) *Attorney, Agent, or Firm* — Weber Rosselli & Cannon LLP

(57) ABSTRACT

A method for using an assembled three-dimensional image to construct a three-dimensional model for determining a path through a lumen network to a target. The three-dimensional model is automatically registered to an actual location of a probe by tracking and recording the positions of the probe and continually adjusting the registration between the model and a display of the probe position. The registration algorithm becomes dynamic (elastic) as the probe approaches smaller lumens in the periphery of the network where movement has a bigger impact on the registration between the model and the probe display.

20 Claims, 13 Drawing Sheets

Related U.S. Application Data continuation of application No. 14/844,181, filed on Sep. 3, 2015, now abandoned, which is a continuation of application No. 11/939,537, filed on Nov. 13, 2007, now Pat. No. 9,129,359.

(60) Provisional application No. 60/865,379, filed on Nov. 10, 2006, provisional application No. 60/867,428, filed on Nov. 28, 2006, provisional application No. 60/887,663, filed on Feb. 1, 2007.

(51) Int. Cl.
| | | |
|---|---|---|
| G06T 7/11 | (2017.01) | |
| G06T 7/155 | (2017.01) | |
| G06T 7/187 | (2017.01) | |
| A61B 34/10 | (2016.01) | |
| G06T 11/20 | (2006.01) | |
| G06T 15/08 | (2011.01) | |
| G06T 17/00 | (2006.01) | |
| A61B 34/00 | (2016.01) | |
| A61B 90/00 | (2016.01) | |

(52) U.S. Cl.
CPC .............. *G06T 7/155* (2017.01); *G06T 7/187* (2017.01); *G06T 7/60* (2013.01); *G06T 11/203* (2013.01); *G06T 15/08* (2013.01); *G06T 17/00* (2013.01); *A61B 2034/107* (2016.02); *A61B 2034/252* (2016.02); *A61B 2090/3762* (2016.02); *G06T 2200/24* (2013.01); *G06T 2207/10081* (2013.01); *G06T 2207/20044* (2013.01); *G06T 2207/20156* (2013.01); *G06T 2207/30061* (2013.01); *G06T 2207/30101* (2013.01)

(58) Field of Classification Search
CPC . G06T 7/0012; G06T 7/11; G06T 7/15; G06T 7/187; G06T 7/60; G06T 11/203; G06T 15/08; G06T 17/00; G06T 2200/24; G06T 2207/10081; G06T 2207/20044; G06T 2207/20156; G06T 2207/30061; G06T 2207/30101
See application file for complete search history.

(56) References Cited

U.S. PATENT DOCUMENTS

| | | |
|---|---|---|
| 5,558,091 A | 9/1996 | Acker et al. |
| 5,729,129 A | 3/1998 | Acker |
| 5,752,513 A | 5/1998 | Acker et al. |
| 5,928,248 A | 7/1999 | Acker |
| 6,016,439 A | 1/2000 | Acker |
| 6,147,480 A | 11/2000 | Osadchy et al. |
| 6,161,032 A | 12/2000 | Acker |
| 6,201,387 B1 | 3/2001 | Govari |
| 6,203,493 B1 | 3/2001 | Ben-Haim |
| 6,211,666 B1 | 4/2001 | Acker |
| 6,226,543 B1 | 5/2001 | Gilboa et al. |
| 6,233,476 B1 | 5/2001 | Strommer et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,366,799 B1 | 4/2002 | Acker et al. |
| 6,373,240 B1 | 4/2002 | Govari |
| 6,427,314 B1 | 8/2002 | Acker |
| 6,453,190 B1 | 9/2002 | Acker et al. |
| 6,484,118 B1 | 11/2002 | Govari |
| 6,558,333 B2 | 5/2003 | Gilboa et al. |
| 6,580,938 B1 | 6/2003 | Acker |
| 6,591,129 B1 | 7/2003 | Ben-Haim et al. |
| 6,618,612 B1 | 9/2003 | Acker et al. |
| 6,650,927 B1 | 11/2003 | Keidar |
| 6,690,816 B2 | 2/2004 | Aylward et al. |
| 6,690,963 B2 | 2/2004 | Ben-Haim et al. |
| 6,788,967 B2 | 9/2004 | Ben-Haim et al. |
| 6,795,521 B2 | 9/2004 | Hsu et al. |
| 6,995,729 B2 | 2/2006 | Govari et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,697,972 B2 | 4/2010 | Verard et al. |
| 7,711,165 B2 | 5/2010 | Lesage et al. |
| 7,817,831 B2 | 10/2010 | Scheuering et al. |
| 7,826,647 B2 | 11/2010 | Capolunghi et al. |
| 7,930,014 B2 | 4/2011 | Huennekens |
| 7,970,189 B2 | 6/2011 | Buelow et al. |
| 8,046,052 B2 | 10/2011 | Verard et al. |
| 8,401,616 B2 | 3/2013 | Verard et al. |
| 9,129,359 B2 | 9/2015 | Averbuch et al. |
| 10,346,976 B2 | 7/2019 | Averbuch et al. |
| 2001/0031919 A1 | 10/2001 | Strommer et al. |
| 2002/0133057 A1 | 9/2002 | Kukuk |
| 2003/0099390 A1 | 5/2003 | Zeng et al. |
| 2004/0097804 A1 | 5/2004 | Sobe |
| 2004/0138548 A1 | 7/2004 | Strommer et al. |
| 2004/0249267 A1 | 12/2004 | Gilboa |
| 2005/0033149 A1 | 2/2005 | Strommer et al. |
| 2005/0107679 A1 | 5/2005 | Geiger et al. |
| 2005/0107688 A1 | 5/2005 | Strommer |
| 2005/0180621 A1 | 8/2005 | Raman et al. |
| 2005/0182295 A1 | 8/2005 | Soper et al. |
| 2005/0182319 A1 | 8/2005 | Glossop |
| 2005/0197566 A1 | 9/2005 | Strommer et al. |
| 2006/0058647 A1 | 3/2006 | Strommer et al. |
| 2006/0064006 A1 | 3/2006 | Strommer et al. |
| 2007/0161854 A1 | 7/2007 | Alamaro |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0287901 A1 | 12/2007 | Strommer et al. |
| 2008/0033452 A1 | 2/2008 | Vetter et al. |
| 2008/0097187 A1 | 4/2008 | Gielen et al. |
| 2008/0132909 A1 | 6/2008 | Jascob et al. |
| 2008/0132911 A1 | 6/2008 | Sobe |
| 2008/0139915 A1 | 6/2008 | Dolan et al. |
| 2008/0147000 A1 | 6/2008 | Seibel et al. |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0247622 A1 | 10/2008 | Aylward et al. |

OTHER PUBLICATIONS

Nakamoto et al. "3D ultrasound system using a magneto-optic hybrid tracker for augmented reality visualization in laparoscopic liver surgery." International Conference on Medical Image Computing and Computer-Assisted Intervention. Springer, Berlin,Heidelberg, 2002. (Year: 2002).

Shahidi et al. "Implementation, calibration and accuracy testing of an image-enhanced endoscopy system." IEEE Transactions on Medical imaging 21.12 (2002): 1524-1535. (Year: 2002).

Kiraly et al. "Three-dimensional Human Airway Segmentation Methods for Clinical Virtual Bronchoscopy", Acad Radiol 2002; 9:1153-1168.

Bricault et al., "Registration of Real and CT-Derived Virtual Bronchoscopic Images to Assist Transbronchial Biopsy", IEEE Transactions on Medical Imaging, vol. 17, No. 5, Oct. 1998.

(56) References Cited

OTHER PUBLICATIONS

Kukuk, M., "A Model-Based Approach to Intraoperative Guidance of Flexible Endoscopy", dissertation Dortmund University, Princeton 2002, Mar. 2003, 195 pages, http://hdl.handle.net/2003/2571.
Geiger et al., "Virtual Bronchoscopy of Peripheral Nodules using Arteries as Surrogate Pathways", Medical Imaging 2005: Physiology, Function, and Structure from Medical Images, Proceedings of SPIE vol. 5746, 352-360.
Schmarak, Itzhak, Gera Strommer and Uzi Eichler, U.S. Appl. No. 10/986,567, filed Nov. 10, 2004, specification and drawings as filed, 81 pages.
WIPO, International Search Report, superDimension, Ltd., dated Nov. 13, 2008, 2 pages, PCT Application No. PCT/IB07/04576, Patent Cooperation Treaty, ISA/US, Alexandria, Virginia.
Kim Do-Yeon, et al: "Automatic navigation path generation based on two-phase adaptive region-growing algorithm for virtual angioscopy", Medical Engineering & Physics, Butterworth-Heinemann, GB, vol. 28, No. 4, May 1, 2006, pp. 339-347.
European Search Report, dated May 26, 2014, Application No. 07873356.5-1906 / 2086399, PCT/IB2007004576.
European Office Action, dated Aug. 27, 2015, for corresponding European Patent Application No. 07873356.5-1906.
European Office Action, dated Jul. 8, 2016, for corresponding European Patent Application No. 07873356.5-1906.
European Office Action, dated Nov. 24, 2016, for corresponding European Patent Application No. 07873356.5-1906.
Geiger et al., "Virtual Bronchoscopy Guidance System for Transbronchial Needle Aspiration", Proc. SPIE 5746, Medical Imaging 2005: Physiology, Function, and Structure from Medical Images, 361-368.
Higgins et al., "3D image fusion and guidance for computer-assisted bronchoscopy", Proc. SPIE 6016, Three-Dimensional TV, Video, and Display IV, 60160A-1-60160-15.
Kiraly et al., "Three-Dimensional Path Planning for Virtual Bronchoscopy", IEEE Transactions on Medical Imaging (vol. 23, Issue: 11, Nov. 2004), 1365-1379.
Helferty et al. "CT-video registration accuracy for virtual guidance of bronchoscopy", SPIEDigitalLibrary.org/conference-proceedings-of-spie; Proceedings of SPIE vol. 5369, Apr. 30, 2004.
Extended European Search Report, dated Sep. 22, 2017, for European Patent Application No. 17183924.4-1906.
European Examination Report issued in Appl. No. EP 17183924.4 dated Aug. 16, 2018 (8 pages).
U.S. Appl. No. 15/635,390, filed Jun. 28, 2017, Patented, U.S. Pat. No. 10,346,976.
U.S. Appl. No. 14/844,181, filed Sep. 3, 2015, Abandoned.
U.S. Appl. No. 11/939,537, filed Nov. 13, 2007, Patented, U.S. Pat. No. 9,129,359.

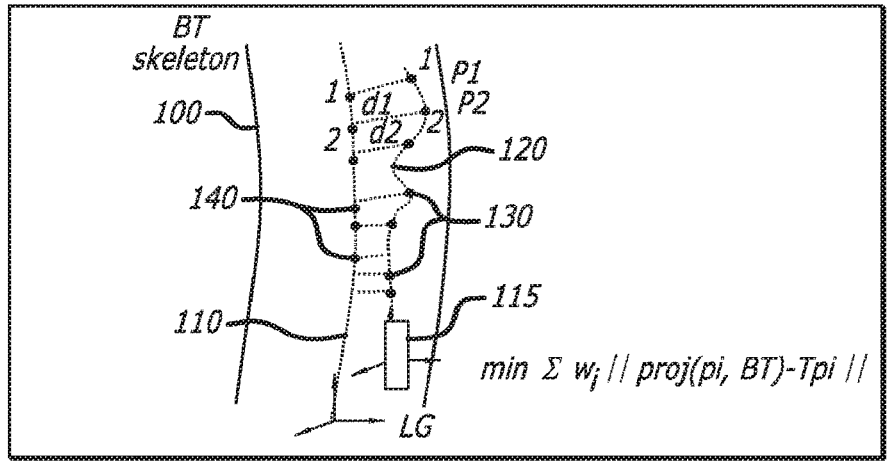

FIG. 1

| The error source | Time characteristics | Comment |
|---|---|---|
| Breathing | VARIABLE | measurable |
| Patient movement | CONSTANT | under control |
| Bronchial tree level | VARIABLE | the uncertainty grows for higher levels of the tree |
| The difference between the diameter of bronchoscope WC or EWC and the bronchial tube | VARIABLE | diminishes as the bronchus diameter gets smaller |
| The difference between the patient position during CT and procedure on setup | CONSTANT | |
| System localization error | CONSTANT | |
| CT segmentation error | CONSTANT | |

FIG. 2

ADAPTIVE NAVIGATION TECHNIQUE FOR NAVIGATING A CATHETER THROUGH A BODY CHANNEL OR CAVITY

RELATED APPLICATIONS

This application is a continuation of U.S. patent application Ser. No. 15/635,390, filed Jun. 28, 2017, which is a continuation of U.S. patent application Ser. No. 14/844,181, filed Sep. 3, 2015, now abandoned, which is a continuation of U.S. patent application Ser. No. 11/939,537, filed Nov. 13, 2007, now U.S. Pat. No. 9,129,359, which claims the benefit of the filing date of provisional U.S. Patent Application No. 60/865,379, filed Nov. 10, 2006; provisional U.S. Patent Application No. 60/867,428, filed Nov. 28, 2006; and provisional U.S. Patent Application No. 60/887,663, filed Feb. 1, 2007, the contents of each of which are incorporated herein by reference. This application also claims the benefit of the filing date of provisional U.S. Patent Application No. 60/865,379, filed Nov. 10, 2006; provisional U.S. Patent Application No. 60/867,428, filed Nov. 28, 2006; and provisional U.S. Patent Application No. 60/887,663, filed Feb. 1, 2007, the contents of each of which are incorporated herein by reference.

BACKGROUND

Breakthrough technology has emerged which allows the navigation of a catheter tip through a tortuous channel, such as those found in the pulmonary system, to a predetermined target. This technology compares the real-time movement of a locatable guide (LG) against a three-dimensional digital map of the targeted area of the body (for purposes of explanation, the pulmonary airways of the lungs will be used hereinafter, though one skilled in the art will realize the present invention could be used in any body cavity or system: circulatory, digestive, pulmonary, to name a few).

Such technology is described in U.S. Pat. Nos. 6,188,355; 6,226,543; 6,558,333; 6,574,498; 6,593,884; 6,615,155; 6,702,780; 6,711,429; 6,833,814; 6,974,788; and 6,996,430, all to Gilboa or Gilboa et al.; and U.S. Published Applications Pub. Nos. 2002/0193686; 2003/0074011; 2003/0216639; 2004/0249267 to either Gilboa or Gilboa et al. All of these references are incorporated herein in their entireties.

One aspect of this background technology pertains to the registration of the CT images that were used, collectively, as a three-dimensional digital map against the actual movement of the LG through the pulmonary system. The user interface shows three separate CT-based images reconstructed by software from x, y, and z directions, simultaneously with the LG location superimposed onto the intersection point of the reconstructed images. If the CT images do not accurately reflect the actual location of the airways, the LG will quickly appear to drift out of the airways as the LG is advanced, thereby diminishing the utility of the navigation system.

Presently, registration points at chosen known landmarks in the central area of lungs are used to register or align the CT based digital map with the patient's chest cavity. These registrations points are first chosen during a planning stage and marked on the internal lung surface. At the beginning of the procedure, the corresponding points are touched and recorded using the LG aided by a bronchoscope in the patient's airways. Doing so allows a computer to align the digital map with the data received from the LG such that an accurate representation of the LG's location is displayed on a monitor.

However, due to various factors, the accuracy of the registration diminishes as the distance between LG and the registration points increases. In other words, the navigation system is less accurate at the periphery of the lungs, where it is most needed. This is due to various factors, two of which are the focus of the present invention. The first factor involves the rigidity of the CT digital image utilized as a digital map by current system while the lung structure is flexible. Second, as the distance increases from the last registration point, errors compound. Compounded errors, coupled with the flexible airways, result in LG that appear to be outside of the airways on the CT images.

As a result of the accumulative inaccuracies, the performance of the existing system is limited. For example, once the bronchoscope is too big to advance, the existing system provides guidance to the user as to whether the LG is being advanced in the direction of the target ignoring the inaccuracies created by the flexibility and internal movement of the living airways. In addition, the guidance instructions to the target are given without regard to the geometries of the airways leading to the target. As a result, user gently advances the LG and watches whether the LG is moving in the direction of the target. If it is not, the LG is retracted and the user "feels" for another airway that may lead to the target rather than see it directly on the CT cross-sections. Hence, two problems arise. First, the LG no longer appears to be located within the airways. Second, the guidance provided does not guide the user along a logical path, it merely provides a general direction to the lesion.

The present invention addresses these two issues by using a unique algorithm to create a BT skeleton, which is a three-dimensional virtual map of the bronchial airways, and by continuously and adaptively matching the LG path to the BT skeleton. Due to the increased accuracy of the BT skeleton and the registration, three-dimensional guidance is extended past the limits of the bronchoscope.

BRIEF DESCRIPTION OF THE DRAWINGS

FIG. 1 is a graphic representation of an algorithm of the present invention;

FIG. 2 is a table showing relative importance of sources of error uncertainty encountered in a method of the present invention;

DETAILED DESCRIPTION

Figure 3:
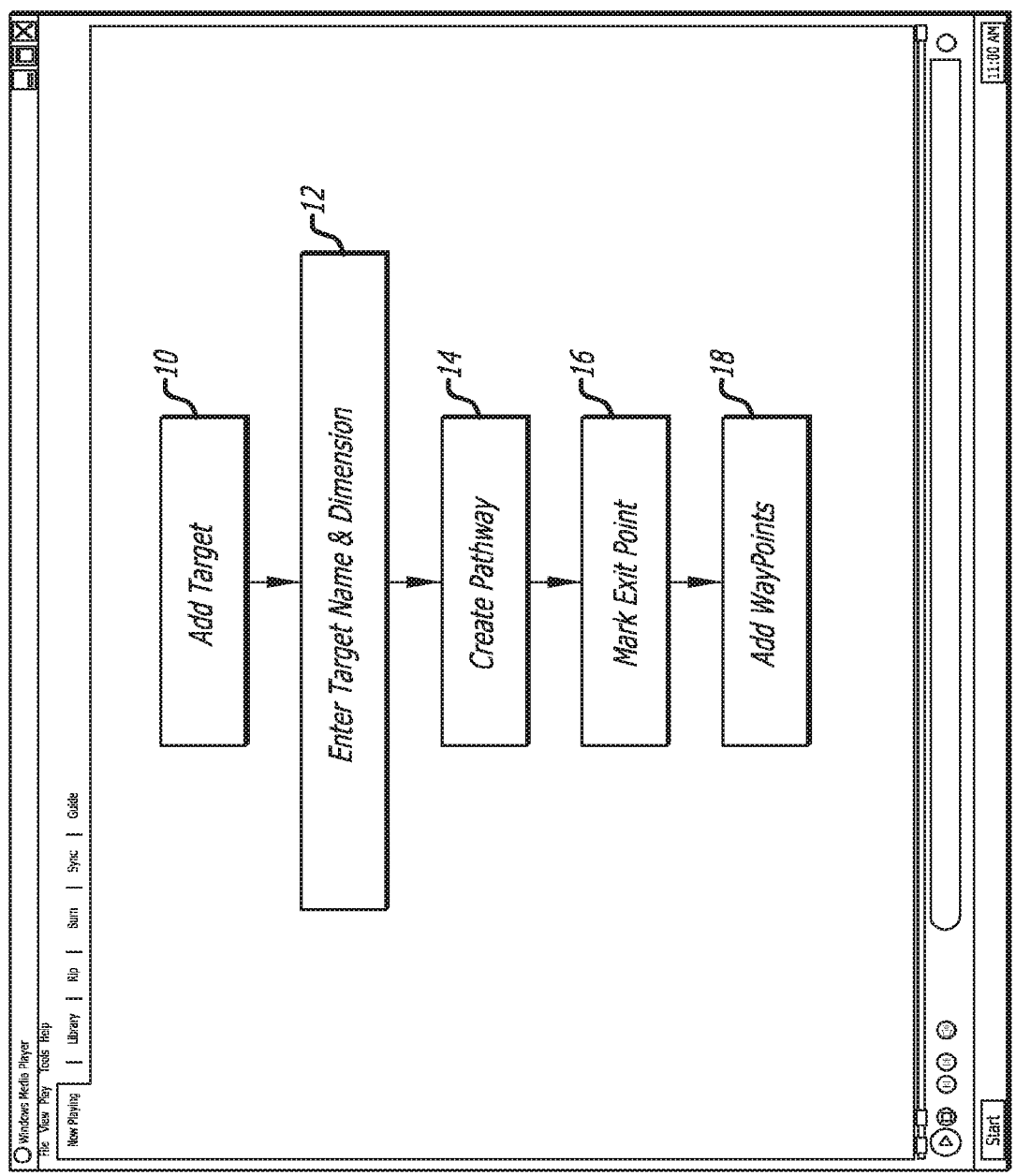
FIG. 3 is a chart showing steps of the pathway generation process of the present invention.

Method of Generating a Pathway to a Target in the Lungs

The present invention includes a unique method of generating a BT skeleton such that an accurate and logical pathway to the target may be formed. Generally, this method begins with an algorithm that automatically detects the trachea inside the CT volume, a three-dimensional image created from a plurality of CT scans, and uses this as a starting point for the generation of the BT. Next, a different segmentation step is applied to mark those voxels of the CT scan that represent air inside the bronchi. Next, the segmented and filtered data is skeletonized—center lines of the perceived airways are defined and used to build an anatomically valid virtual model of the airways.

More specifically, the method of generating a pathway to a target inside the lungs is outlined as follows:

1. Bronchial Tree Generation

Bronchial tree generation is a fully automatic process that runs in the background and is thus transparent to the user while working with the application software.

2. Automatic Seed Point Detection

Automatic seed point detection is an algorithm that detects the trachea by searching for a tubular object having the density of air in the upper region of the CT volume. The center of gravity of the found tubular object is defined as a seed point for further segmentation.

3. Segmentation: Lung's Air Differentiation

Segmentation is a process based on a Region Growing Algorithm (see p. 73 of Handbook of Medical Imaging, Processing and Analysis, Isaac N. Bankman, Academic Press, 2000, incorporated by reference herein in its entirety.), which defines and displays the bronchial airways from the CT volume images of the human chest. The purpose of the Region Growing Algorithm is to construct homogeneous regions of points connected to the starting seed point and satisfying the following condition: Hounsfield values (HU) in all of these points are lower than a predefined maximum threshold value.

The implemented process is fully automatic, iterative and consists of several steps:

3.1 Anatomical Feature Segmentation:

The purpose is to mark (or segment) the portion of voxels (voxel=Volume Pixel) of a substance inside a recognizable feature of the lumen network This recognizable feature is used as a starting point. For example, in the case of the airways of the lungs being the lumen network, the trachea is preferred for selection as the anatomical feature. Hence the portion of voxels representing air inside the trachea, avoiding the bubbles caused by noise and artifacts inside the CT images is marked. Region growing with a high threshold value is then applied inside the volume for this purpose. If the blood vessels constitute the lumen network of interest, for example, the aorta could be used as the anatomical feature.

3.2 Adaptive Threshold Detection for Region Growing Algorithm:

3.2.1 Starting from the boundary of the previously segmented area from step 3.1, multiple iterations of a region growing algorithm are performed. With each iteration the following steps occur:

3.2.1.1 A threshold value is defined and all voxels lower than the threshold value are deemed to be containing only air and are thus segmented. This process is iterative, but growth rate and geometry are not considered.

3.2.1.2 After the segmentation process is completed for that iteration, the whole number of segmented voxels inside the lungs stemming from the seed point are recorded.

3.2.2 Next the threshold value is increased and the next iteration is performed. After this iteration is completed, the number of segmented voxels between the current iteration and the previous one are compared.

3.2.3 Each iteration should result in a greater number of connected voxels because the threshold value increases with each iteration. Increasing the threshold value means that more voxels are considered as air.

3.2.4 If the difference in the number of segmented voxels between two consecutive iterations has increased significantly, this event is considered as leakage. Practically it means that somewhere the bronchi wall was "broken" by segmentation and in addition to the air inside the lung, the outside lung air is now connected to the segmented volume.

So a conclusion is drawn that the current threshold is too high and the threshold value from the previous iteration is used.

3.2.5 Finally segmentation is performed with the selected threshold. This time the segmentation result is added to the step 1 and stored. This will be used as a starting point for the next step.

3.3 Leakage Control:

This is required in order to improve the results of the region-growing algorithm using the adaptive threshold local values by segmenting additional areas. The technique of section 3.2 is applied for every boundary point (point located on tissue) of previously segmented area.

3.4 Geometry Control Wave Propagation:

This is described in the article, "Hybrid Segmentation and Exploration of the Human Lungs, IEEE Visualization 2003, Dirk Bartz, Dirk Mayer, Jan Fischer, Sebastian Ley, Anxo del Ro, Stef Thust, Claus Peter Heussel, Hans-Ulrich Kauczor, and Wolfgang Straβer, the entirety of which is incorporated by reference herein. This article enables additional improvement over previous steps using higher threshold levels due a mechanism of geometrical parameter control of growing branches.

3.5 "Template Matching":

This approach is based on the aforementioned article by Bartz et al. and evaluates the candidate area below templates with the values of uncertain density (between −950 HU and −775 HU). This is organized in two stages; the first stage establishes templates that are used in the second stage to evaluate the local voxel neighborhood. First, 2D template matching applies 2D region growing starting from the boundary voxels of the previous segmentations. The thresholds are varied—from the upper threshold of the uncertain density value interval (−775 HU)—until the number of selected voxels is below the critical limit, since it can be assumed that they did not leak out. Based on this selected voxel area, circular templates of varying sizes is generated. In the second stage, we apply a 2D region growing. The shape of each connected segmented area is compared with set of circular templates from the 1st stage. The positive comparison result is then selected and added to the segmentation.

3.6 Bubble Filter:

Finally a bubble filter is applied. A bubble filter is a combination of morphological dilation and erosion operations. It is used to eliminate small non-segmented regions (bubbles) from the final segmented area. These bubbles appear due to the noisy nature and artifacts of CT images.

4. Skeletonization and Feature Calculation

Skeletonization and feature calculation refers to the extraction of centerlines of previously segmented bronchi, the building of a valid anatomical hierarchy of bronchial airways, the calculation of bronchi diameters and geometric features, and the surface generation for each segmented bronchi. The following steps are involved:

4.1 Thinning Algorithm:

The iterative object reduction technique described in the article, A Sequential 3D Thinning Algorithm and Its Medical Applications, K'alm'an Pal'agyi, Erich Sorantin, Emese Balogh, Attila Kuba, Csongor Halmai, Bal'azs Erd"ohelyi, and Klaus Hausegger, 17th Int. Conf. IPMI (2001) 409-415 the entirety of which is incorporated herein by reference, and is used to convert the previously segmented airways into a geometric skeleton representation.

4.2 Branches and Node Points Detection:

A map of all the skeleton voxels is generated, so for each voxel we have a list of neighbor voxels. Voxels with three or more neighbors are considered to be "node points". The voxels with two neighbors are considered as points on the branch. The entire voxel map is rearranged as a graph with nodes and branches.

4.3 Filtering of False Branches:

This involves the following steps:

4.3.1 Identify and remove disconnected branches.

4.3.2 Resolve graph loops by removing the longest branch of two branches connected to a common node.

4.3.3 Remove relatively short leaves in the graph, considering them a result of a leakage.

4.3.4 Remove leaves that are relatively close to each other.

4.4 Convert Graph to Tree:

Find the root point on the graph as one nearest to the seed point found in 1. The graph is converted to a binary tree. Branches are approximated by polynomials.

4.5 Branch Labeling: Logical and Hierarchical:

This is performed according to the technique described in the article, Automated Nomenclature Labeling of the Bronchial Tree in 3D-CT Lung Images, Hiroko Kitaoka from Osaka University, Yongsup Park, Juerg Tschirren, Joseph Reinhardt, Milan Sonka, Goeffrey McLennan, and Eric A. Hoffman from University of Iowa, Lecture Notes in Computer Science, T. Dohi and R. Kikinis, Eds. Amsterdam, The Netherlands: Springer-Verlag, Oct. 2002, vol. 2489, pp. 1-11, the entirety of which is incorporated by reference herein.

4.6 Automatic Evaluation of Tree Quality

Tree quality is evaluated based on the recognition of the following main parts of the skeleton:

4.6.1 right lower lobe (RLL) and right middle lobe (RML), 4.6.2 right upper lobe (RUL)

4.6.3 left upper lobe (LUL)

4.6.4 left low lobe (LLL)

Branch numbers and branch length features are calculated separately for each area and compared to statistical model or template of acceptable anatomy to evaluate the tree quality.

4.7 Extraction of External Surfaces of Bronchial Tubes:

Modification of a widely known method called "marching cubes" is used to extract airways surface from volumetric CT data.

5. Planning the Path to the Peripheral Target

This process plans the pathway from the trachea entrance to the target area.

As the CT resolution limits the final quality of automatically generated bronchial tree described in 1., the user is enabled to perform the pathway fine tuning.

6. Target Marking

The planning software is used for planning the bronchoscopic procedure of navigating to suspect lesion (target) inside the human lungs.

The target center and target dimensions are manually marked with the planning software.

7. Pathway Semi-Automatic Generation

At this point there are both the automatically generated bronchial tree and the target. However the target may be located out of the tree. This happens for several reasons, including:

The target may lay inside the tissue

Some small bronchi may be missing from the automatically generated tree due to the CT resolution limitations.

Therefore, a gap is created and shall be completed manually. Using both the interactive display of the bronchial tree and CT cross-sections, the user manually selects the point on the bronchial tree that shall be connected to the target center. This is called the "exit point".

The pathway from the trachea to the "exit point" is automatically generated. In addition the original tree is extended by a linear branch that connects the "exit point" and the target center.

8. Pathway Fine Tuning

Using the CT cross-section user is optionally able to define split the automatically created linear branch into segments, defining the intermediate waypoints by intuitive graphic user interface.

9. On-Path Guidance

On-Path guidance is designed to keep the locatable tool inside the planned path (displayed in green). In this approach the path is approximated by an automatically generated 3D poly-line. The poly-line segments are connected with the vertex. Each vertex is defined as an intermediate target in our system. During navigation when an intermediate target is reached, it disappears and the next intermediate target appears and becomes the current target. The mathematical vector connecting the actual location of the locatable tool with the incoming intermediate target is calculated. This mathematical vector is translated to the locatable tool operation through the following instructions set:

9.1 Push Forward\Backward 9.2 Set the specific rotation angle 9.3 Apply bending ON\OFF.

Additional methods are contemplated that may improve the accuracy of the BT generated by the aforementioned method. First, arterial blood vessels may be tracked and used to regenerate missing airway data from the CT. Because the arterial blood vessels from the heart to the lungs terminate at the alveoli, deductions can be made regarding the location of the bronchioles leading to the alveoli. Second, an anatomic atlas created from data derived from multiple lung models can be used to evaluate and complete the generated BT geometry. Though every lung is unique, each has common characteristics portrayed in an anatomic atlas. This information can be used to deduce and fill in missing BT geometry data.

Accuracy may also be improved by utilizing multiple sensors. For example, acquiring the location and orientation data from the electromagnetic system may be performed using multiple external and/or multiple internal sensors. These could be located on the extended working channel (EWC), the locatable guide (LG), the bronchoscope, or attached to the interior of the lung.

The location and orientation data acquired from the electromagnetic system, regardless of the number of sensors used, may be used to complete any missing branches from the BT due to limitation in CT resolution.

It is also contemplated that flexibility may be added to the generated BT structure by utilizing multiple sets of CT data, each representing different points in the patient's breathing cycle. For example, three CT scans could be taken, one at the peak inhalation point of a normal breathing cycle, one at the peak exhalation point of a normal breathing cycle, and one midway in between. External sensor positions may optionally be noted to record chest positions during these various "snapshots" taken with the CT. Noting the differences in positions of the bronchial features in each of the three locations provides information on the individual movement paths of the features during the breathing cycle. The movement paths can be estimated by connecting the three recorded points. Once the flexible BT is generated, external position sensors on the patient can be used to detect the patient's breathing cycle, and for determining the corresponding locations of the various bronchial features along their respective movement paths.

This simulated flexibility can be calculated and used individually for each patient or, if it is desired to minimize the cost and radiation exposure of multiple CT scans, can be used as a model for other patients. Several models can be recorded and kept on file for later matching to patients as a function of anatomic location, patient dimension, gender age, phase of breathing cycle, etc.

Adaptive Navigation Method

The present invention also provides unique method of continually and adaptively matching the automatically generated BT skeleton to the patient during the procedure. Generally, this method records consecutive locations of the LG as it is advanced through the airways. Because it is known that the LG travels through airways, the BT skeleton is continually matched such that the LG appears in an airway. Hence, the accuracy of the navigation improves, rather than degrades, as the LG is advanced.

More specifically, this method is outlined as follows:
1. General Considerations Adaptive Skeleton Navigation method is developed to detect the current location of a locatable guide ("LG") being introduced through a patient's bronchial airway on a map of the bronchial tree obtained using a CT Scan. This is achieved by constant and adaptive correlation between the two data sets: the bronchial airway tree map and the sensor data history. The correlation above is performed via two steps:
1) Adaptive Skeleton-Based Registration.
2) Adaptive Skeleton-Based Navigation.

Note that these steps, described in detail below, may be performed recursively.

2. The Adaptive Skeleton-Based Registration Algorithm

This section includes the description of the proposed algorithm of adaptive skeleton-based registration. Registration, generally, is a method of computing transformations between two different coordinate systems. Here, the goal is to register the bronchial tree (BT) skeleton to the locatable guide (LG) path.

2.1 Requirements:
2.1.1 The registration accuracy improves as the locatable guide gets closer to the lower levels of the lumen network (e.g. bronchial tree) and the peripheral target.
2.1.2 The registration is updated continuously and adaptively, depending on the location of the LG in the bronchial tree. The LG path is a history of LG locations as the LG is manipulated through the bronchial tree.

2.2 Technical Issues:
2.2.1 Geometrically paired 3D/3D points (or other objects) from the BT skeleton and the LG path are the registration basis (see, e.g. pairs 1-1' and 2-2' in FIG. 1).
2.2.2 The registration is continuous and adaptive. "Continuous" means that the registration is continually (iteratively) re-computed as new LG path points are obtained. "Adaptive" means that different paired points, weights, and registration methods are used as the LG advances towards the target.
2.2.3 The registration consists of two main phases: global rigid registration followed by local deformable registration. Deformable registration is only performed in the lower levels of the bronchial tree and near the peripheral target. The idea is to start with rigid registration when the bronchus is wide and switch to constrained and localized deformable registration when the diameter of the probe is close to the diameter of the bronchus and the bronchus becomes flexible.
2.2.4 Global rigid registration is performed with the sophisticated Weighted Iterative Closest-Point (WICP) method with outlier removal. The pairing is performed by using the weighted function of position distance and orientation difference of the paired objects. The optimization function is the weighted sum of paired point distances. The parameters to determine are the weight function and the number of points to use.
2.2.5 Local non-rigid registration is performed with a constrained elastic registration method in which paired points are connected with springs and the optimization function is the springs' potential energy.
2.2.6 The LG path is not monotonic therefore it should be judiciously sampled and windowed so that the path data is of good quality.
2.2.7 The accuracy or the registration improves when user-defined landmark points are acquired with the LG.

3. Registration Algorithm
3.1 Input: BT Path from CT Scan, Initial Registration Guess, LG Locations (Stream)
3.2 Output: Rigid Registration (6 Parameters)+Local Deformation Map
3.3 Algorithm Method—FIG. 1 shows an outline of the actual bronchus 100, with a line showing the BT skeleton 110 and a second line 120 showing the path of the LG 115 through the bronchus 100. The path 120 of the LG 115 will be used to register the BT skeleton 110 to the actual bronchus 100, such that the BT skeleton, seen by the physician, is an accurate representation of the actual bronchus location. The LG path 120 includes a plurality of actual LG locations 130. Corresponding projected points 140 are shown on the BT skeleton 110. The differences between the actual points 130 and the projected points 140 are represented with lines (e.g. d1, d2) between the skeleton 110 and the path 120. With continued reference to FIG. 1, the registration algorithm is described:

3.3.1 Perform first registration with an initial registration guess. Apply transformation to the BT. Use the registration results, obtained from the initial registration phase.
3.3.2 While enroute to the target:
3.3.2.1 Obtain new stream of LG locations from sensor.
3.3.2.2 Perform cleaning, decluttered and classification (weighting) on the stream of LG locations.
3.3.2.3 Perform selection of the LG location stream according to the optimization decision and registration history.
3.3.2.4 Project the selected LG location segments/points on BT skeleton to obtain paired segments/points. The projection is performed by optimizing the following criteria.
3.3.2.4.1 Minimal Distance relative to the local bronchi diameter.
3.3.2.4.2 Minimal Orientation difference.
3.3.2.4.3 The matched branch points (p1, p2, etc.) on the path.
3.3.2.5 Global rigid registration: weight paired points and obtain new rigid registration with WICP. Apply new computed transformation to the LG.
3.3.2.6 Local deformable registration: when appropriate (only when the Extended Working Channel—EWC and bronchus diameters are close to each other), perform deformable registration on chosen window. Apply transformation to the BT local branches. The usefulness of this correction shall be determined empirically.
3.3.3 Validation that the registration doesn't get worse as a result of noise sensor data:
3.3.3.1 Perform LG history classification by breathing averaging or specific phase. Define the maximal deviation from the initial registration.

3.3.3.2 Make sure that the LG history is mostly inside the bronchus.

4. The Adaptive Skeleton-Based Navigation 4.1 The Basic Idea

The implementation of navigation shall be similar to the navigation with the map. Similar tasks have been implemented in GIS (Geographic Information System) systems, such as PDA (Personal Digital Assistant) systems for blind people. It has been proven by that data topology is important for higher navigation accuracy. However our problem is significantly different from above due to the bronchial tree flexibility and movement.

4.2 The needed input information 4.2.1 current sensor position and orientation data 4.2.2 The history of sensor position and orientation data 4.2.3 The registration (matrix) history.

4.2.4 The sources of navigation uncertainty

FIG. 2 is a table that presents the sources of error uncertainty in the order of importance, with the values having a higher contribution into the final error at the top of the table. The error prediction model based on this table shall be developed to predict the navigation uncertainty. The assumed prediction model is the sphere around the computed location whose radius includes the localization uncertainty. The radius of this sphere is a function of time and location.

In Use

FIGS. 3-13 show several stages of the aforementioned methods. First, the pathway generation process is described. FIG. 3 is a chart showing the pathway generation steps 10-18. FIGS. 4-13 are representations of the user interface that guides a user through these steps during the planning stage prior to a procedure.

Figure 4:
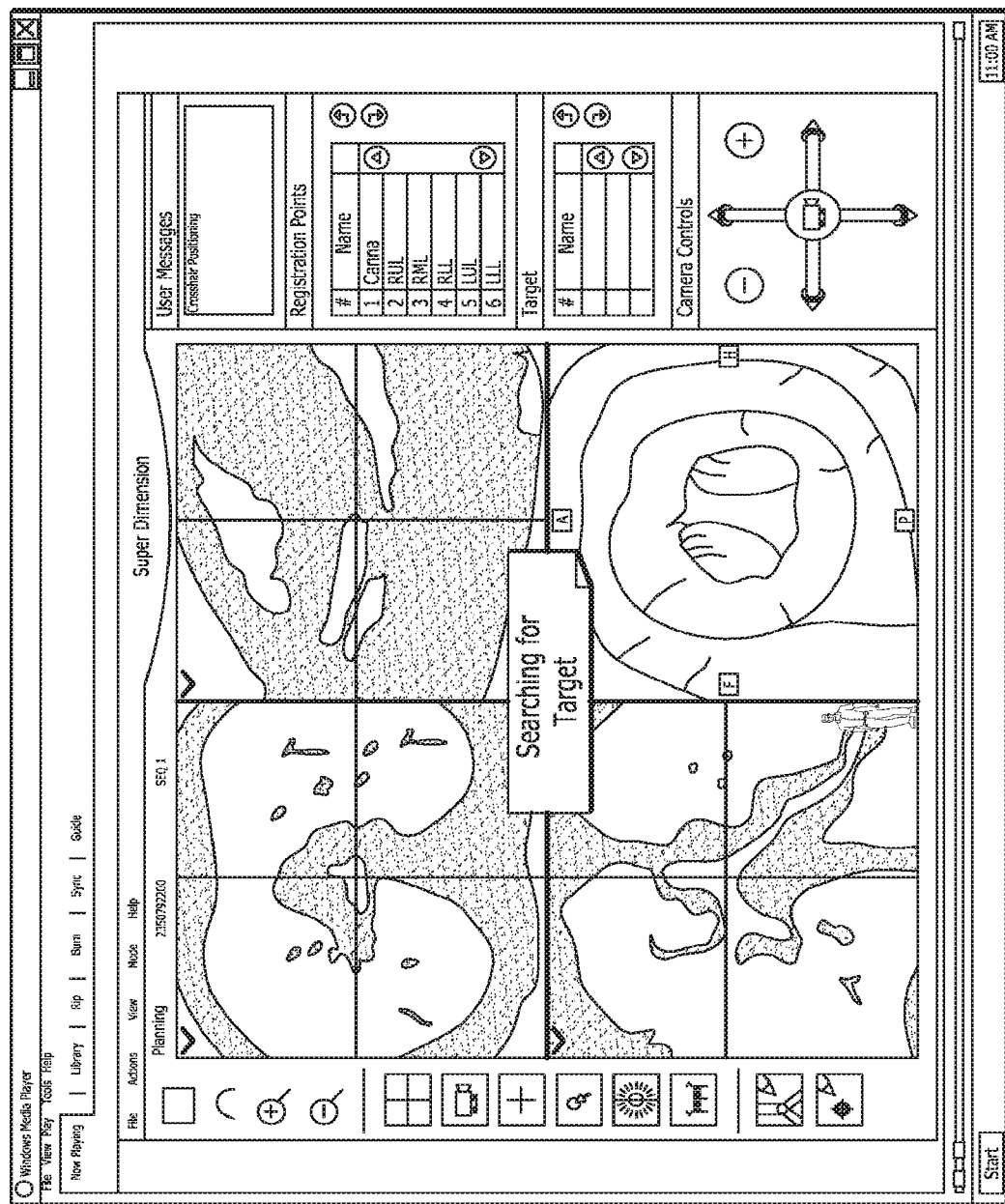
FIGS. 4-13 are screen captures of the user interface during the pathway generation process of the present invention.

A user engaged in the first step 10, adding a target, is shown in FIG. 4. The upper left quadrant is a CT cross-section reconstructed from the viewpoint of the patients feet looking toward his head. The lower left quadrant is a CT cross-section reconstructed from the front of the patient such that the plane is parallel to the table on which the patient is lying. The upper right quadrant is a cross-section reconstructed from CT directed at the side of the patient. Cross-hairs mark the targeted spot that is the intersection of all the cross-sections reconstructed from CT. Each of the CT cross-sections shows a projection of a small camera that represents the virtual bronchoscope inside the CT volume. The lower right quadrant is a virtual bronchoscopy view of the targeted spot from within the BT as though seen from the camera. Notably, the display shown in the Figures is just an example. If the user feels the need for different views, the system allows for views from any angle to be displayed in the various quadrants. Hence, the system is completely configurable and customizable to the user's preferences.

Figure 5:
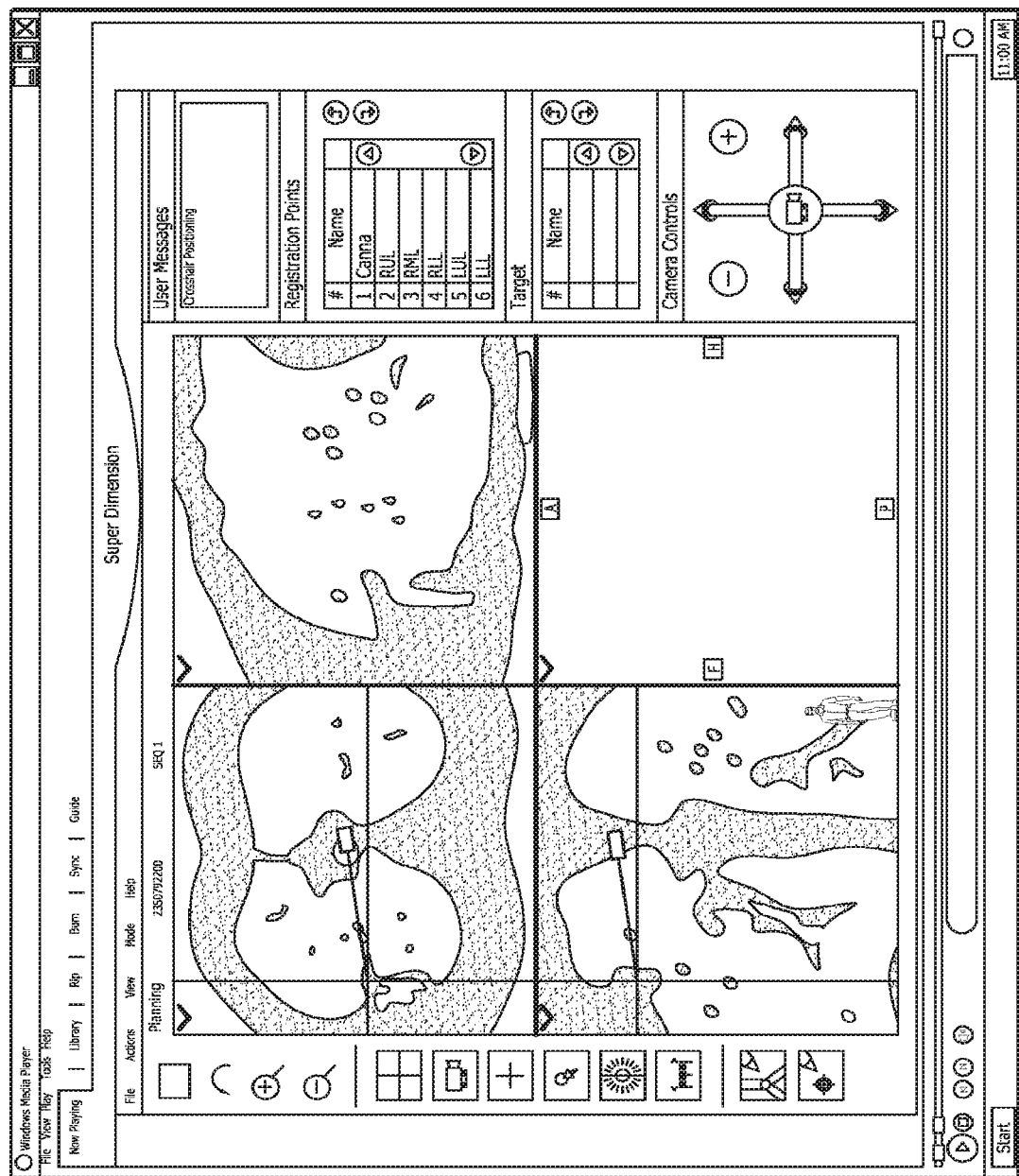
Figure 6:
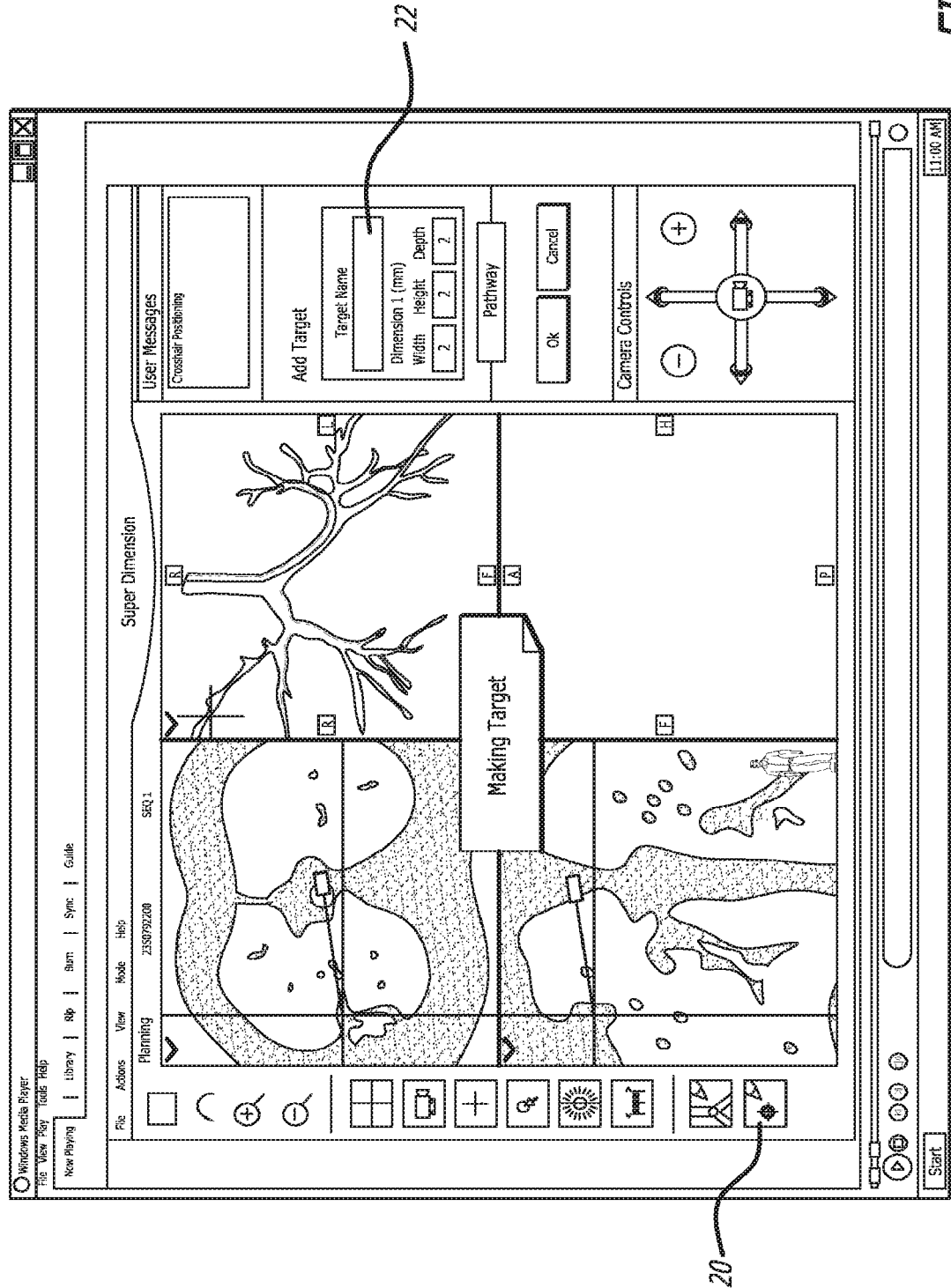

In FIG. 5, the user has selected the target and the message "Crosshairs positioning" appears in the user messages box in the upper right corner of the user interface. Selecting the very bottom button 20, marks the target, as seen in FIG. 6. The user may enter a target name in the box 22, thus beginning the next step of FIG. 3.

Figure 7:
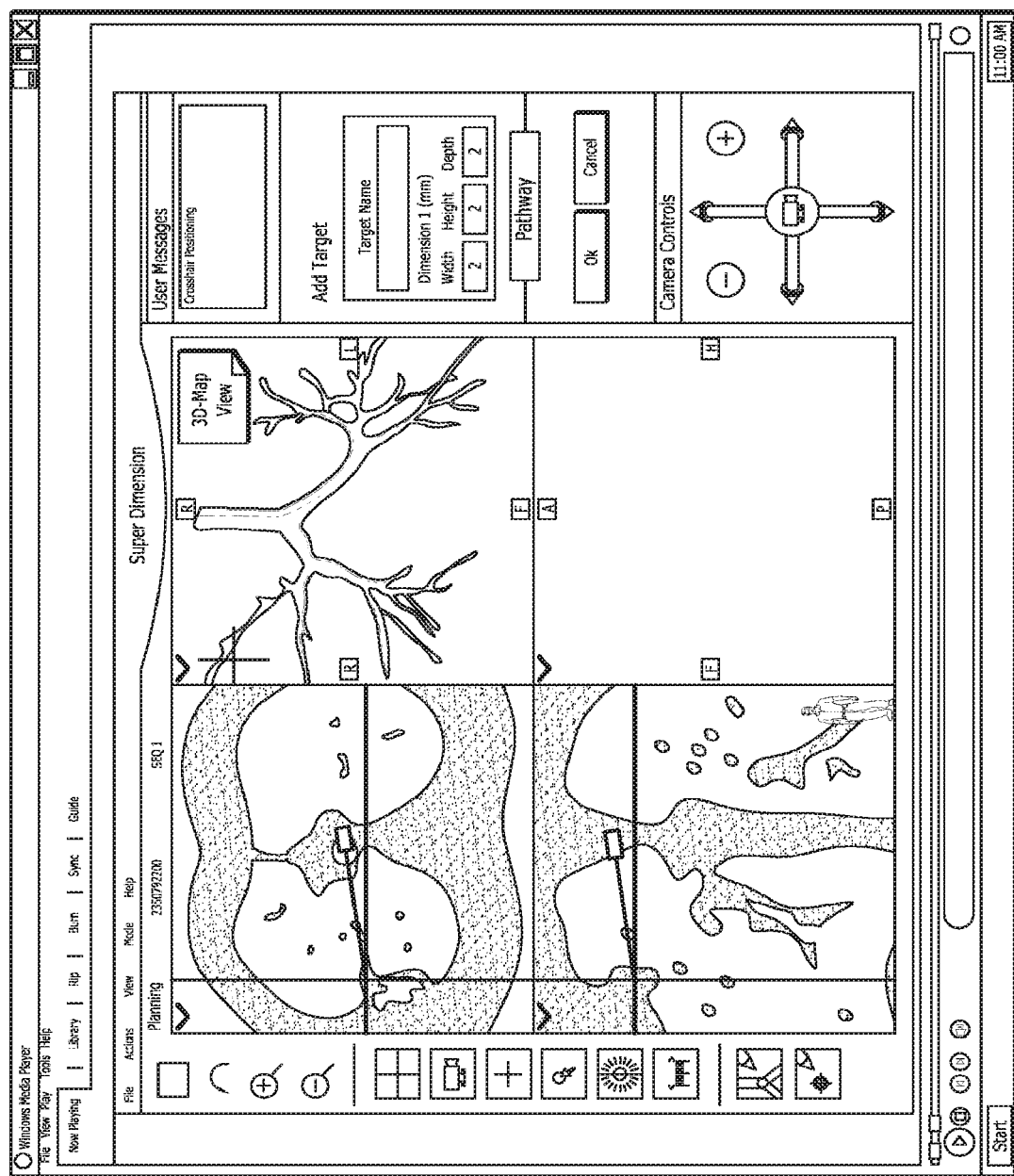

FIG. 7 illustrates that the user has the option of displaying the BT skeleton in the upper right quadrant, rather than the side view.

Figure 8:
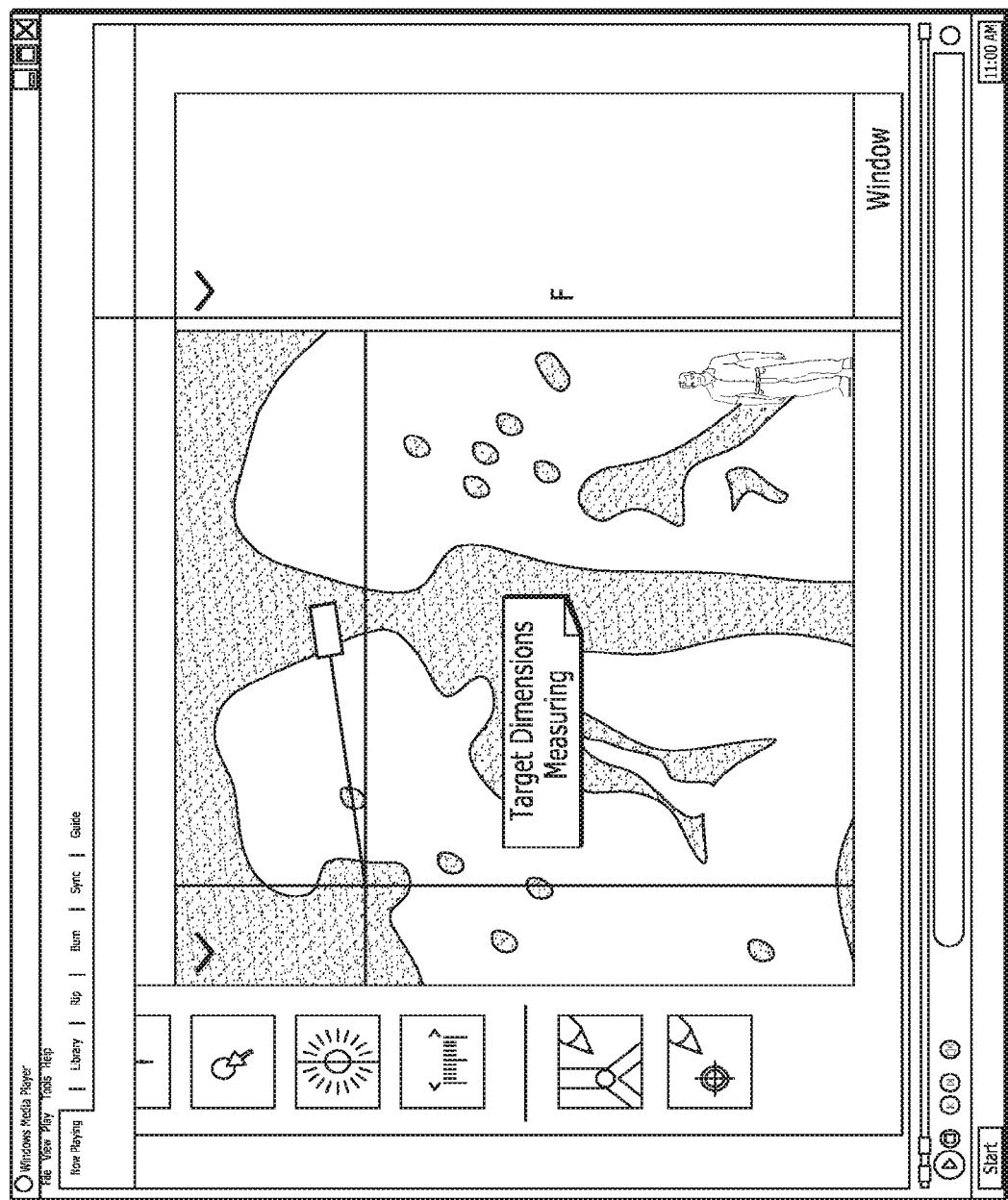
Figure 9:
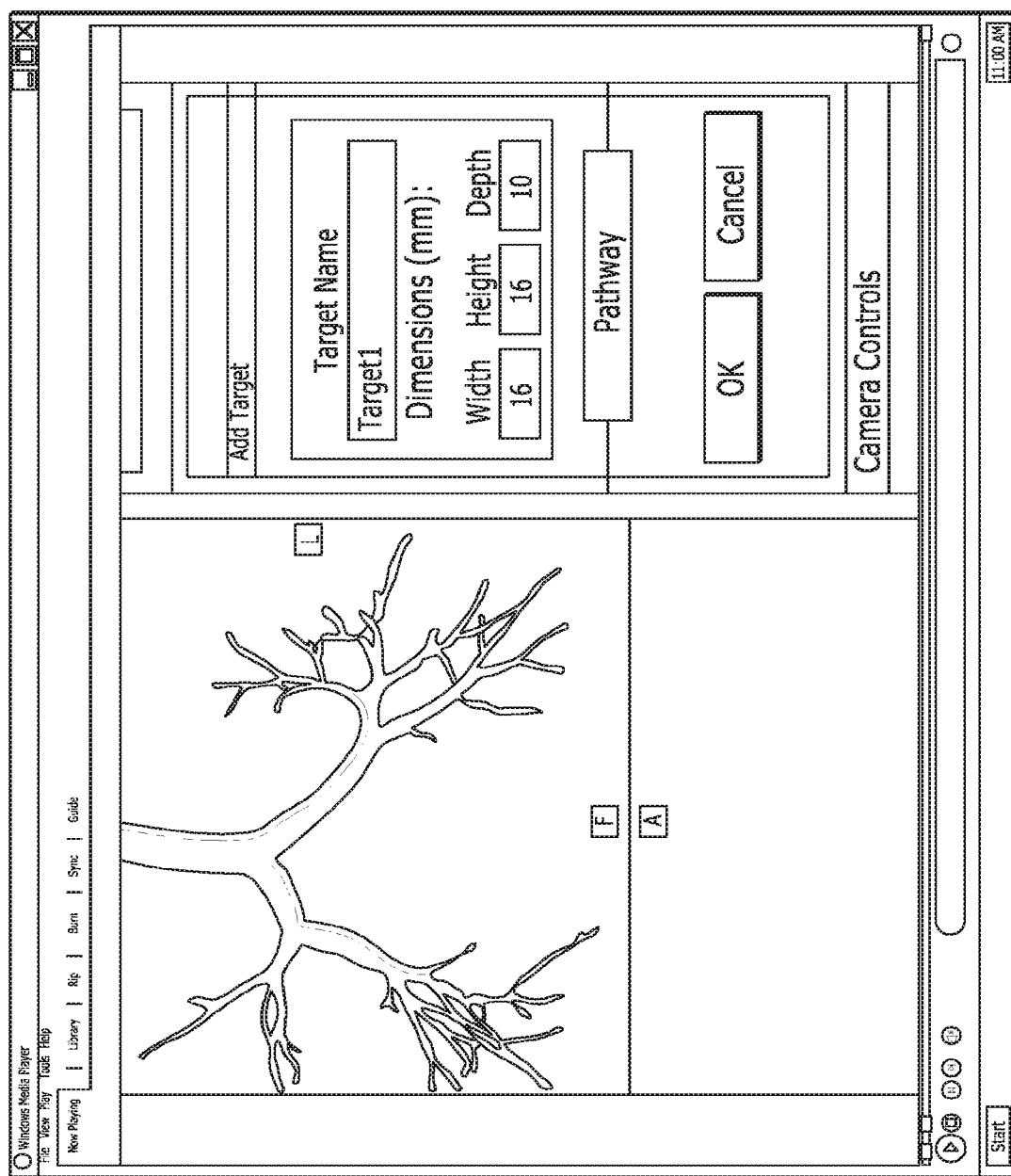

In FIG. 8, the selected target is being measured. In FIG. 9, a name has been assigned to the target.

Figure 10:
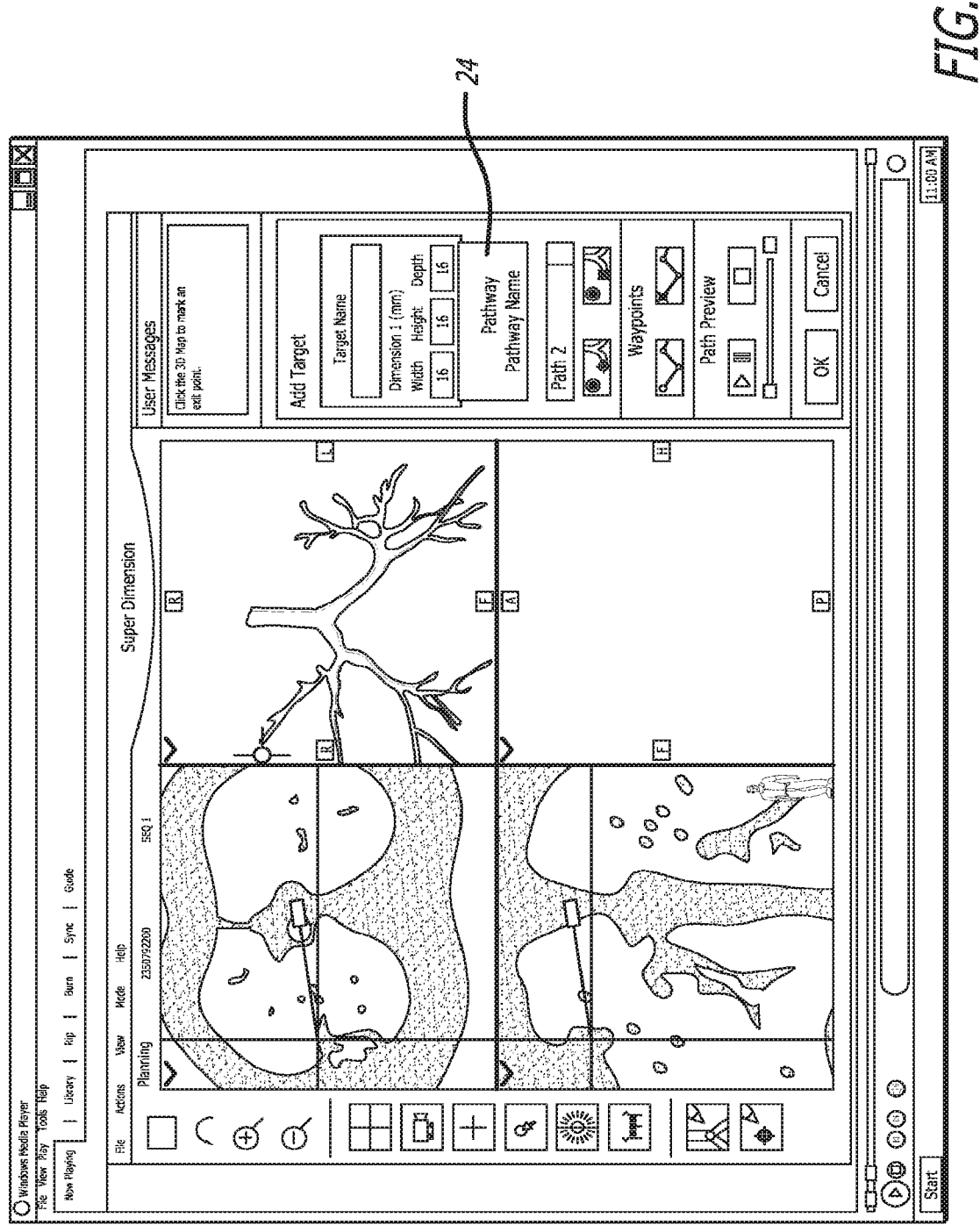

The pathway creation step 14 begins in FIG. 10. The pathway button 24 is pressed and a name is given to the pathway.

Figure 11:
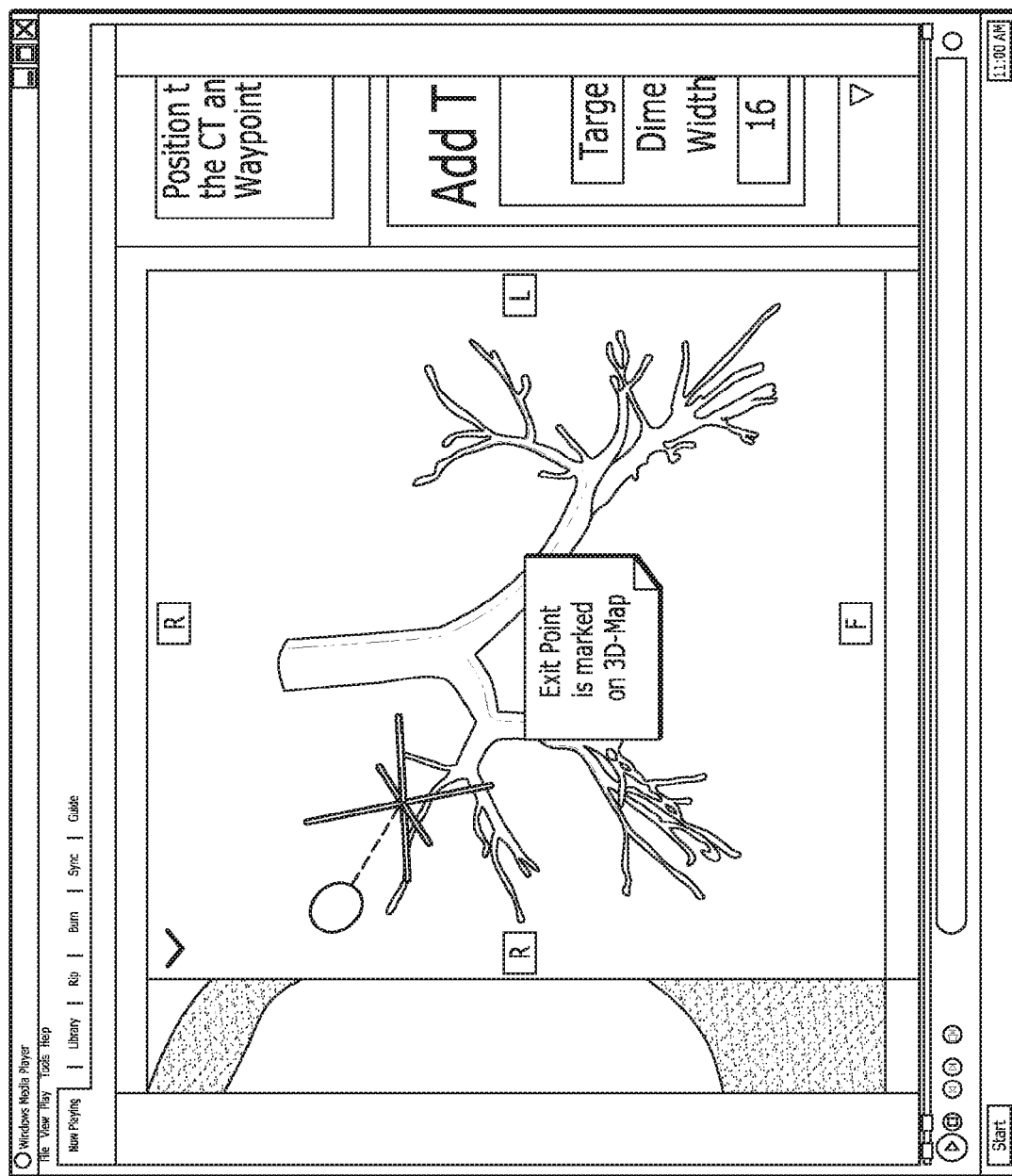

FIG. 11 shows the exit point marking step 16. The exit point is marked on the map, from which a straight line will be drawn to the target. Having identified a destination (exit point), the pathway can be determined.

Figure 12:
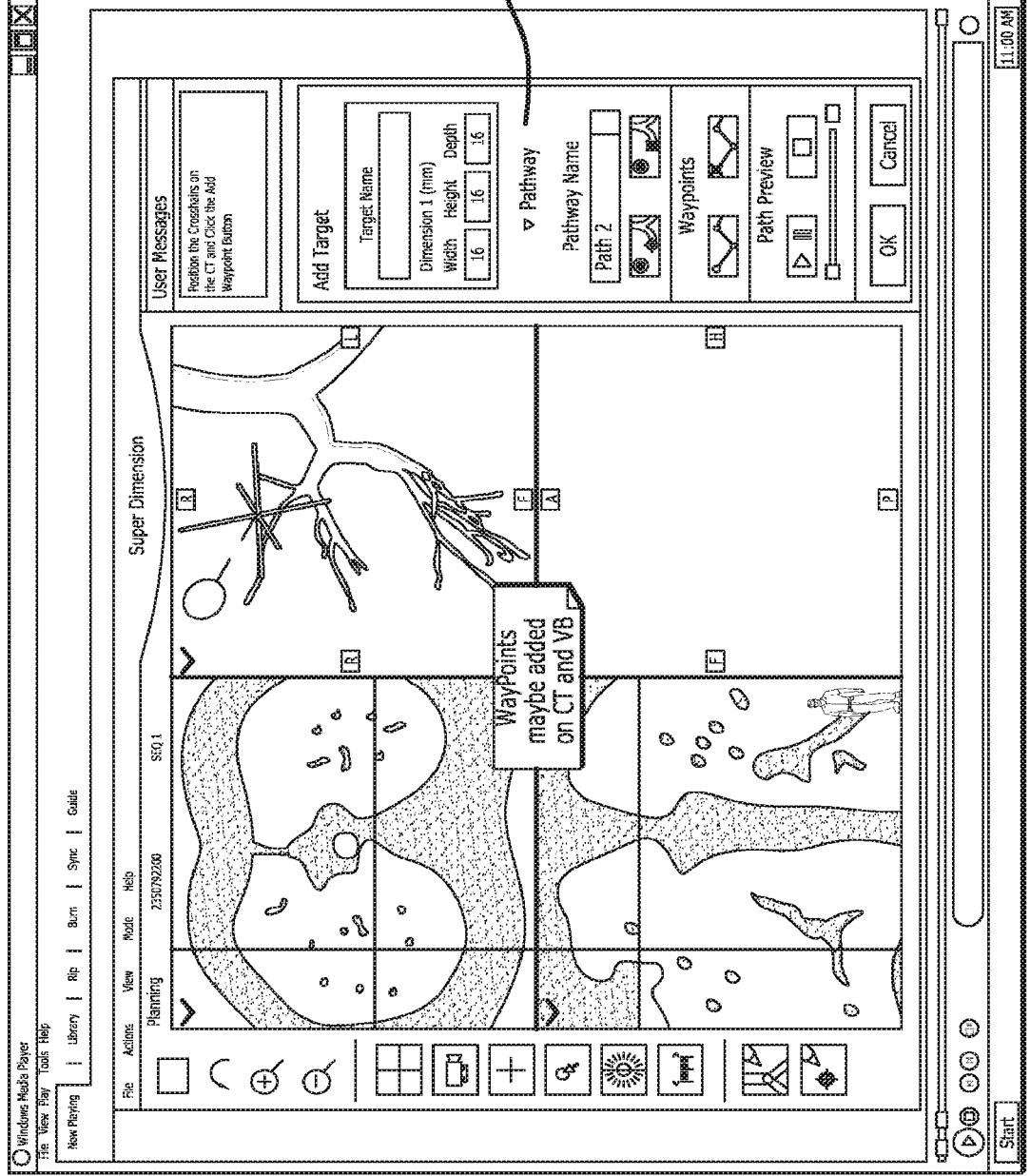
Figure 13:
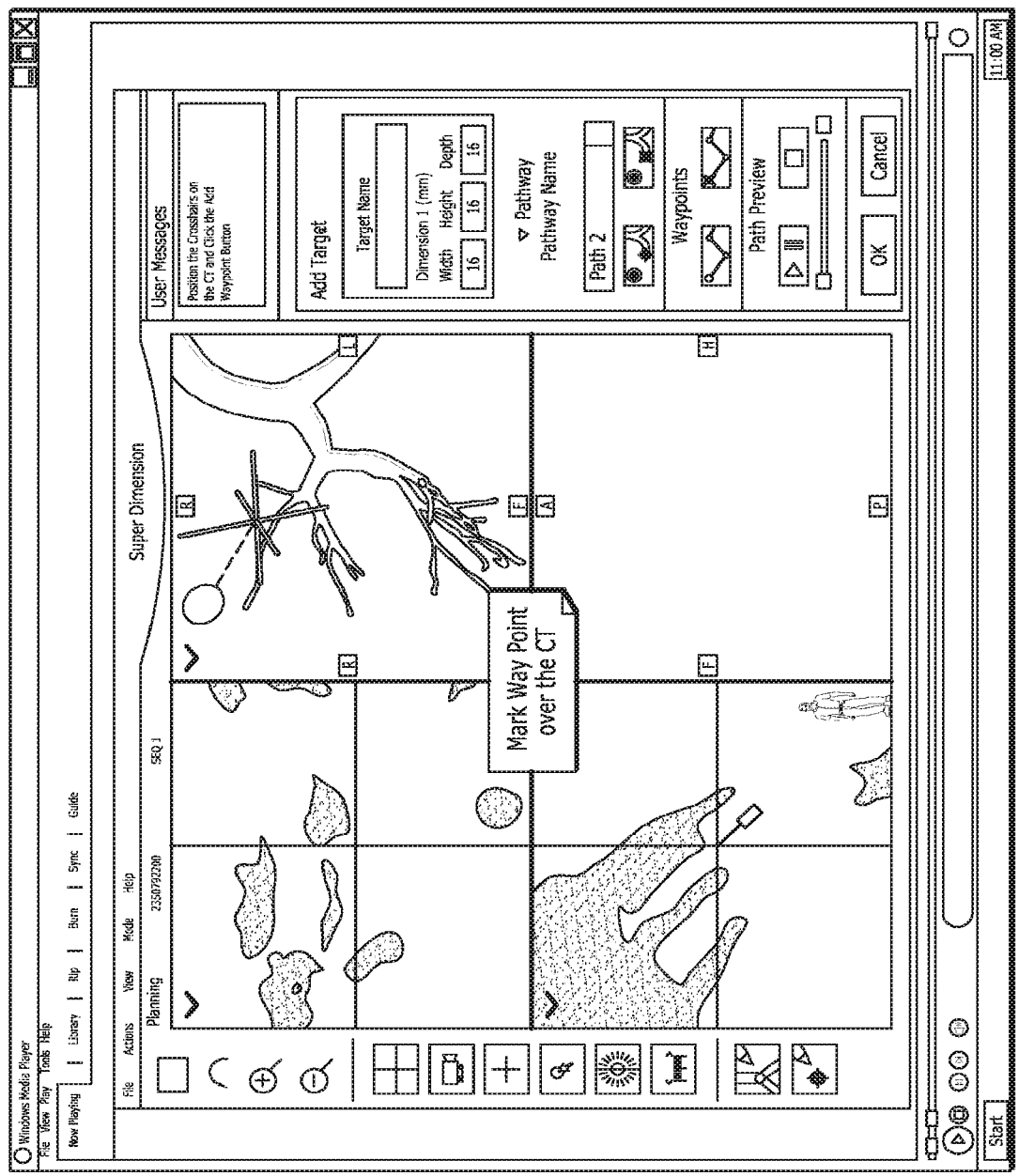

Next the add waypoints step 18 is completed, as seen in FIGS. 12 and 13. Waypoints may be added to assist the user to follow the pathway by marking the turns enroute to the exit point.

Figure 14:
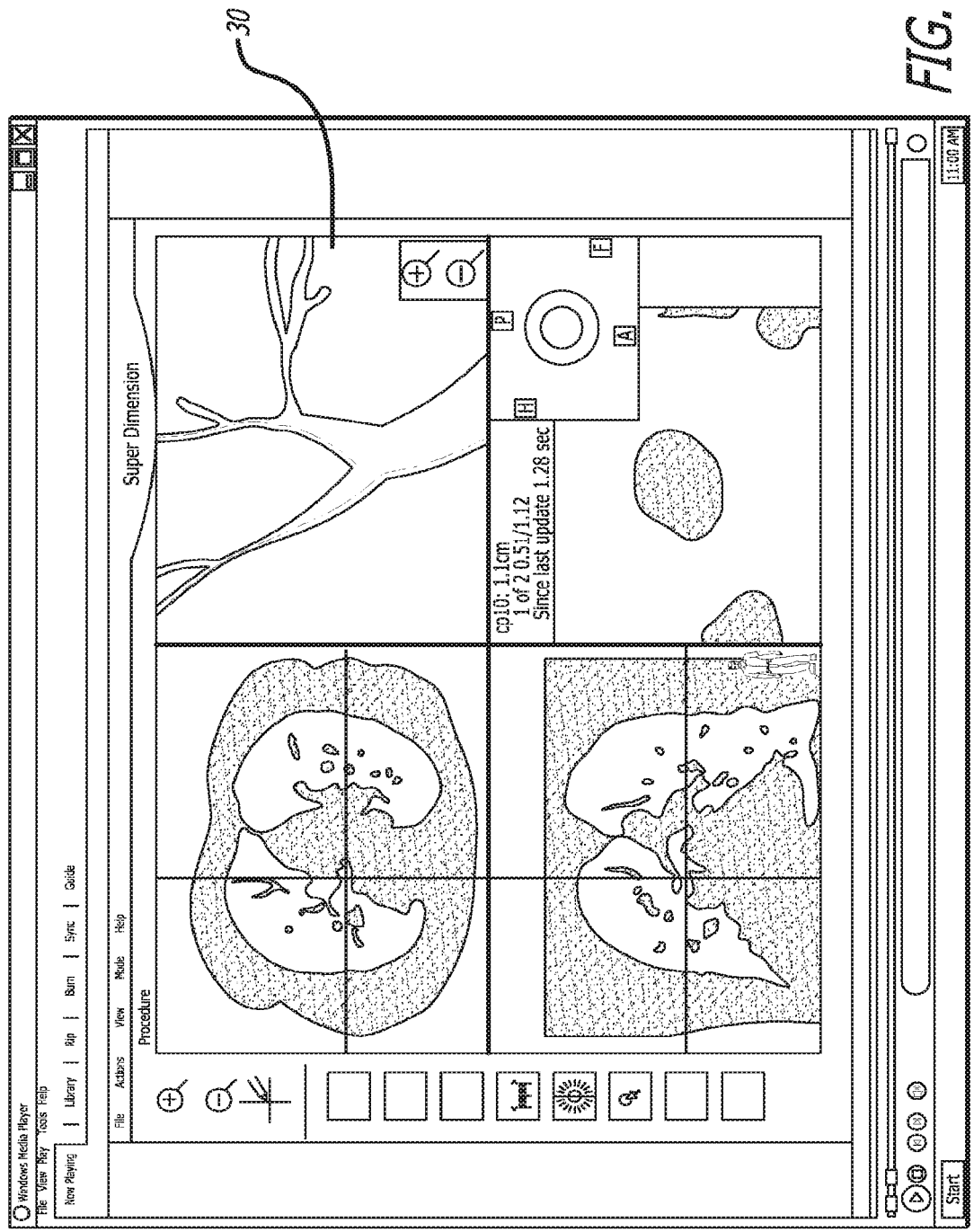
FIG. 14 is a screen capture of the user interface of the present invention while a procedure is being performed on a patient.

FIG. 14 shows the user interface during a procedure being conducted on a patient. In the upper right quadrant, the three-dimensional BT skeleton is shown with an LG indicator 30 visible. The aforementioned AN algorithm ensures that the BT skeleton remains registered with the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof. Additionally, it should be noted that any additional documents referenced in the attached documents are incorporated by reference herein in their entireties.

We claim:

1. A system for registering a computer model of a lumen network to a lumen network of a patient, comprising:
   a probe configured to be navigated within a patient's lumen network;
   a sensor coupled to the probe; and
   a computing device operably coupled to the sensor and including a memory and a processor, the processor configured to:
      establish a path of the probe within the patient's lumen network based on data points received by the processor from the sensor; and
      register a path shape on the computer model of the lumen network to the probe path based on a diameter of a lumen in which the probe is located relative to a diameter of the probe.

2. The system according to claim 1, wherein the processor is configured to remove outlier data points from the data points received by the processor from the sensor.

3. The system according to claim 1, wherein the computing device is operably coupled to a display configured to display the computer model of the lumen network, and the processor is configured to update the displayed computer model of the lumen network based on the registering of the path shape on the computer model of the lumen network to the probe path.

4. The system according to claim 1, wherein the processor is configured to:
   cause an indicator of the sensor location on the computer model of the lumen network to be displayed; and
   update a location of the displayed indicator based on the registering of the path shape on the computer model of the lumen network to the probe path.

5. The system according to claim 1, wherein the processor is configured to match a lumen of the computer model of the lumen network to the probe path.

6. The system according to claim 1, wherein the processor is configured to rigidly register the path shape on the computer model of the lumen network to the probe path.

7. The system according to claim 1, wherein the processor is configured to deformably register the path shape on the computer model of a lumen network to the probe path.

8. The system according to claim 1, wherein the processor is configured to:
rigidly register the path shape on the computer model of the lumen network to the probe path when the diameter of the lumen in which the sensor is located is large relative to the diameter of the probe; and
deformably register the path shape on the computer model of the lumen network to the probe path when the diameter of the lumen in which the sensor is located approaches the diameter of the probe.

9. The system according to claim 1, wherein the processor is configured to:
determine a plurality of projected points along a pathway through the computer model of the lumen network;
pair at least a portion of the data points received from the sensor with at least a portion of the plurality of projected points; and
adjust the computer model of the lumen network based on the pairing.

10. The system according to claim 1, wherein the data points received from the sensor include data corresponding to at least one of a current position of the sensor or an orientation of the sensor.

11. The system according to claim 1, wherein the sensor is disposed on a distal portion of the probe.

12. The system according to claim 1, wherein the processor is configured to:
generate the path shape from the patient's trachea to an exit point; and
extend the patient's lumen network by a linear branch that connects the exit point to a target within the patient's lumen network.

13. The system according to claim 1, wherein the processor is configured to:
skeletonize the computer model of the lumen network by extracting centerlines from the computer model of the lumen network; and
identify branch points in the computer model of the lumen network at intersections of the centerlines.

14. A system for registering a computer model of a lumen network to a lumen network of a patient, comprising:
a probe including a sensor configured to be navigated within a patient's lumen network; and
a computing device operably coupled to the sensor and including a memory and a processor, the processor configured to:
receive, from the sensor, data points pertaining to a location of the probe within the patient's lumen network;
remove outlier data points from the data points received from the sensor;
establish a path of the probe within the patient's lumen network based on the data points having the outlier data points removed; and
register the computer model of the lumen network to the probe path based on at least one of a diameter of a lumen in which the probe is located or a diameter of the probe.

15. The system according to claim 14, wherein the processor is configured to register the computer model of the lumen network to the probe path based on the diameter of the lumen in which the probe is located relative to the diameter of the probe.

16. The system according to claim 14, wherein the processor is configured to register a path shape on the computer model of the lumen network to the probe path.

17. The system according to claim 14, wherein the data points received from the sensor include data corresponding to at least one of a current position of the sensor or a current orientation of the sensor.

18. A system for registering a computer model of a lumen network to a lumen network of a patient, comprising:
a probe including a sensor configured to be navigated within a patient's lumen network;
a computing device operably coupled to the sensor and including a memory and a processor, the processor configured to:
establish a path of the probe within the patient's lumen network based on data points received by the processor from the sensor; and
register a path shape on the computer model of the lumen network to the probe path based on at least one of a diameter of a lumen in which the probe is located or a diameter of the probe.

19. The system according to claim 18, wherein the processor is configured to register the path shape on the computer model of the lumen network to the probe path based on the diameter of the lumen in which the probe is located relative to the diameter of the probe.

20. The system according to claim 18, wherein the processor is configured to remove outlier data points from the data points received by the processor from the sensor.

* * * * *